US009155511B2

(12) United States Patent
Ohta et al.

(10) Patent No.: US 9,155,511 B2
(45) Date of Patent: Oct. 13, 2015

(54) BREAST IMAGE CAPTURING APPARATUS (71) Applicant: FUJIFILM CORPORATION, Tokyo (JP)

(72) Inventors: Yasunori Ohta, Ashigarakami-gun (JP); Takao Kuwabara, Ashigarakami-gun (JP); Yasuko Yahiro, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 139 days.

(21) Appl. No.: 13/966,486

(22) Filed: Aug. 14, 2013

(65) Prior Publication Data
US 2013/0331682 A1 Dec. 12, 2013

Related U.S. Application Data (63) Continuation of application No. PCT/JP2012/001267, filed on Feb. 24, 2012.

(30) Foreign Application Priority Data

Feb. 25, 2011 (JP) .................................. 2011-039272

(51) Int. Cl.
A61B 6/04 (2006.01)
A61B 6/10 (2006.01)
(Continued)

(52) U.S. Cl.
CPC ............. *A61B 6/502* (2013.01); *A61B 6/022* (2013.01); *A61B 6/025* (2013.01); *A61B 6/107* (2013.01); *A61B 6/4452* (2013.01); *A61B 6/467* (2013.01); *A61B 6/0414* (2013.01); *A61B 6/542* (2013.01)

(58) Field of Classification Search
CPC ...... A61B 6/03; A61B 6/0414; A61B 6/0435; A61B 6/10; A61B 6/107; A61B 6/502; A61B 6/022; A61B 6/025; A61B 6/4452; A61B 6/46
USPC .............................. 378/4, 11, 25, 26, 37, 145
See application file for complete search history.

(56) References Cited

U.S. PATENT DOCUMENTS

2004/0161075 A1* 8/2004 Amitani ........................... 378/37
2007/0036265 A1* 2/2007 Jing et al. ........................ 378/37
(Continued)

FOREIGN PATENT DOCUMENTS

EP 1 759 637 A2 3/2007
FR 2 882 246 A1 8/2006
(Continued)

OTHER PUBLICATIONS

International Search Report Issued in PCT/JP2012/001267, mailed on May 22, 2012.
(Continued)

*Primary Examiner* — Robert Kim
*Assistant Examiner* — David E Smith
(74) *Attorney, Agent, or Firm* — Birch, Stewart, Kolasch & Birch, LLP (57) ABSTRACT In a breast image capturing apparatus having an arm section for moving a radiation source in a left-right direction in front of a subject, providing a shielding member for preventing radiation from being applied to the face of the subject on an arm section, and supporting the shielding member movably relative to the arm section when the face of the subject is abutted to the shielding member and fixedly relative to the arm section when the face of the subject is not abutted to the shielding member.

7 Claims, 5 Drawing Sheets (51) Int. Cl.
*A61B 6/00* (2006.01)
*A61B 6/02* (2006.01)

(56) References Cited

U.S. PATENT DOCUMENTS

2007/0116176 A1   5/2007   Meer et al.
2009/0323892 A1*  12/2009  Hitzke et al. .................... 378/37
2010/0183119 A1*  7/2010   Ludwig et al. ................. 378/37

FOREIGN PATENT DOCUMENTS

FR    2882246 A1 *   8/2006
JP    2006-231054 A   9/2006
JP    2010-167131 A   8/2010
WO    WO 2010/066517 A1   6/2010

OTHER PUBLICATIONS

Extended European Search Report dated Sep. 4, 2014, issued in corresponding European Patent Application No. 12750302.7.

* cited by examiner

BREAST IMAGE CAPTURING APPARATUS

CROSS-REFERENCE TO RELATED APPLICATIONS

This application is a continuation of PCT International Application No. PCT/JP2012/001267 filed on Feb. 24, 2012, which claims priority under 35 U.S.C. 119(a) to Application No. 2011-039272 filed on Feb. 25, 2011 in Japan, all which are hereby expressly incorporated by reference in the present application.

TECHNICAL FIELD

The present invention relates to a breast image capturing apparatus that applies radiation to a breast of a subject from two different image capturing directions in order to capture a radiation image of the breast with respect to each image capturing direction, and more particularly to a breast image capturing apparatus provided with a face guard for preventing radiation from being applied to the face of the subject.

BACKGROUND ART

Heretofore, it is known that a stereovision can be obtained through the use of parallax by displaying a plurality of images in combination. Such a stereoscopically viewable image (hereinafter, stereoscopic image or stereo image) is generated based on a plurality of images having a parallax obtained by imaging the same subject from different directions.

The generation of such stereoscopic images is performed not only in the fields of digital cameras and televisions but also in the field of radiation image capturing. That is, it is practiced that a plurality of radiation images having a parallax is obtained by applying radiation to a subject from different directions and detecting radiation transmitted through the subject with respect to each direction using a radiation image detector, and a stereoscopic image is generated based on these radiation images. The generation of the stereoscopic image in the manner described above allows a radiation image having a sense of depth to be observed, that is, it is possible to observe a radiation image more suitable for diagnosis. As one of radiation image capturing apparatuses that generates such stereoscopic images, a mammography apparatus is proposed.

DISCLOSURE OF INVENTION

In a mammography apparatus for capturing a breast image, radiation is applied from a radiation source unit installed above the subject to a breast of the subject. Here, in order to prevent radiation emitted from the radiation source unit from being applied to the face of the subject, for example, a face guard is provided against the radiation source unit.

It is often the case that the subject forced to have an uncomfortable body posture with a breast being fixed barely maintains a stable body posture by tightly pressing the head of the subject against the face guard.

In the mammography apparatus that captures a stereoscopic image by applying radiation from different image capturing directions as described above, however, it is necessary to move the radiation source unit in a left-right direction viewed from the subject. This will cause the face guard to be moved to a position away from the face position of the subject along with the movement of the radiation source unit, so that the subject is unable to maintain the body posture and may result in an unstable dangerous state.

Consequently, Japanese Unexamined Patent Publication No. 2006-231054 proposes the provision of a drive means for moving the face guard in a direction opposite to the moving direction of the radiation source unit so that the face guard remains at the face position of the subject. As for the drive means, for example, an electric roller for sliding the face guard, an electric gear, or the like are proposed.

It is undesirable that the face guard is configured to be invariably moved along with the movement of the radiation source unit as in the apparatus described in Japanese Unexamined Patent Publication No. 2006-231054. Because, if that is the case, the face guard is moved unnecessarily, for example, at the time of maintenance or calibration in which no radiation image capturing is performed, thereby disturbing the maintenance or calibration, as well as being undesirable from the viewpoint of durability.

Further, an electric roller or gear is used for making the face guard movable in Japanese Unexamined Patent Publication No. 2006-231054, but a more simple mechanism for making the face guard movable is desirable from the viewpoint of cost.

In view of the circumstances described above, it is an object of the present invention to provide a breast image capturing apparatus provided with a face guard capable of stabilizing the body posture of a subject by maintaining the position of the face guard at the face position of the subject and improving user-friendliness and durability by a simple arrangement and without moving the face guard unnecessarily.

A breast image capturing apparatus of the present invention is a breast image capturing apparatus, including a radiation application section which includes an arm section for moving a radiation source in a left-right direction in front of a subject and applies radiation to a breast of the subject from different image capturing directions above the breast through the movement of the radiation source by the arm section, and a radiation image detector that detects a radiation image generated through the application of radiation by the radiation application section with respect to each of the image capturing directions, wherein:

a shielding member for preventing the radiation from being applied to the face of the subject is provided on the arm section; and the shielding member is configured so as to be movably supported relative to the arm section when the face of the subject is abutted to the shielding member and fixedly supported relative to the arm section when the face of the subject is not abutted to the shielding member.

The breast image capturing apparatus of the present invention described above may include a latch for controlling the movement of the shielding member by engaging with a predetermined member and the latch may be a latch that does not engage with the member when the face of the subject is abutted to the shielding member and engages with the member when the face of the subject is not abutted to the shielding member.

Further, the breast image capturing apparatus of the present invention described above may include a sensor for detecting that the face of the subject is in contact with the shielding member and a latch drive for driving the latch according to a result of the detection by the sensor.

The latch may be a latch whose engagement with the member is released by a force generated by the abutment of the face of the subject to the shielding member.

The breast image capturing apparatus of the present invention described above may include an elastic member that expands or contracts according to whether or not the face of the subject is abutted to the shielding member and the latch may be a latch that engages with or disengages from the member by the expansion or contraction of the elastic member.

The shielding member may be a shielding member that, while the face of the subject is abutted to the shielding member, does not move from the position of the face of the subject.

Further, a grooved member having a groove that engages with the latch may be fixedly mounted in the arm section.

A breast image capturing apparatus of the present invention is a breast image capturing apparatus, including a radiation application section which includes an arm section for moving a radiation source in a left-right direction in front of a subject and applies radiation to a breast of the subject from different image capturing directions above the breast through the movement of the radiation source by the arm section, and a radiation image detector that detects a radiation image generated through the application of radiation by the radiation application section with respect to each of the image capturing directions, wherein:

a shielding member for preventing the radiation from being applied to the face of the subject is provided on the arm section; and the shielding member is configured so as to be movably supported relative to the arm section when the radiation source is in a power-on state and fixedly supported relative to the arm section when the radiation source is in a power-off state.

According to a breast image capturing apparatus of the present invention, a shielding member for preventing the radiation from being applied to the face of the subject is provided on the arm section, and the shielding member is movably supported relative to the arm section when the face of the subject is abutted to the shielding member and fixedly supported relative to the arm section when the face of the subject is not abutted to the shielding member. This allows the position of the shielding member to be maintained at the face position of the subject when the face of the subject is abutted to the shielding member, i.e., while radiation image capturing is performed, whereby the body posture of the subject may be stabilized. On the other hand, when the face of the subject is not abutted to the shielding member, i.e., during maintenance or calibration in which no radiation image capturing is performed, the shielding member is not moved unnecessarily, whereby user-friendliness and durability may be improved.

Further, in the breast image capturing apparatus of the present invention described above, if a latch is provided for controlling the movement of the shielding member by engaging with a predetermined member and the latch is configured not to engage with the member when the face of the subject is abutted to the shielding member and to engage with the member when the face of the subject is not abutted to the shielding member, the movement of the shielding member may be controlled with a simple arrangement and cost effectively.

According to the breast image capturing apparatus of the present invention, the shielding member is configured so as to be movably supported relative to the arm section when the radiation source is in a power-on state and fixedly supported relative to the arm section when the radiation source is in a power-off state. This allows the position of the shielding member to be maintained at the face position of the subject when the radiation source is in a power-on state, i.e., while radiation image capturing is performed, whereby the body posture of the subject may be stabilized, while when the radiation source is in a power-off state, i.e., during maintenance or calibration in which no radiation image capturing is performed, the shielding member is not moved unnecessarily, whereby user-friendliness and durability may be improved, as in the case described above.

BEST MODE FOR CARRYING OUT THE INVENTION

Figure 1:
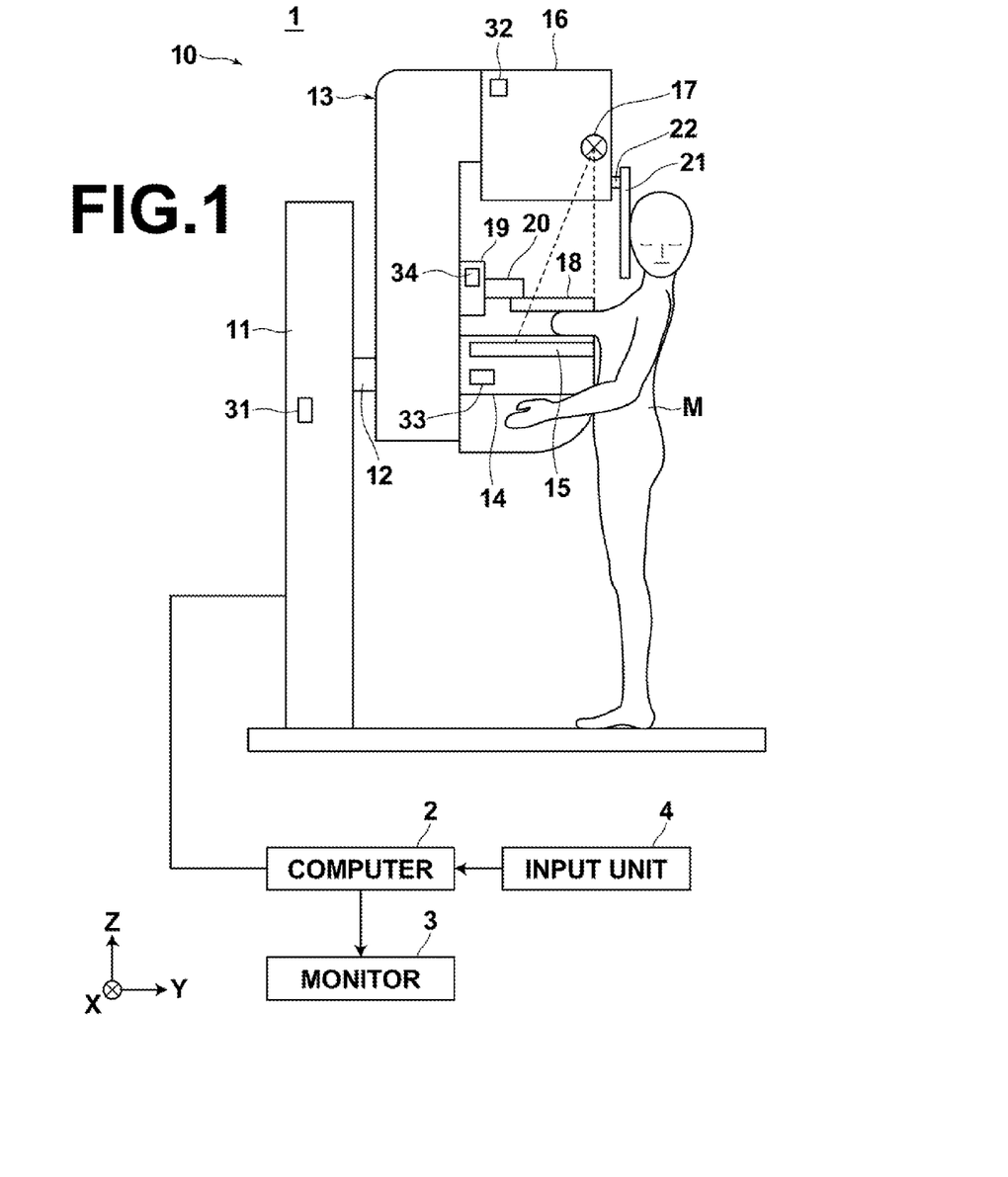
FIG. 1 is a schematic configuration diagram of a breast image capturing and display system that uses an embodiment of the breast image capturing apparatus of the present invention.

Hereinafter, a breast image capturing and display system that uses an embodiment of the breast image capturing apparatus of the present invention will be described with reference to the accompanying drawings. FIG. 1 illustrates a schematic configuration of the entire breast image capturing and display system of the present embodiment.

As illustrated in FIG. 1, the breast image capturing and display system 1 of the present embodiment includes a breast image capturing apparatus 10, a computer 2 connected to the breast image capturing apparatus 10 with a monitor 3 and an input unit 4 connected to the computer 2.

As illustrated in FIG. 1, the breast image capturing apparatus 10 includes a base 11, a rotary shaft 12 which is movable in up-down directions (Z directions) with respect to the base 11 and rotatable, and an arm section 13 coupled to the base 11 by the rotary shaft 12.

The arm section 13 has a shape of letter C with an image capturing platform 14 on which a breast is placed at one end and a radiation source unit 16 at the other end attached so as to face the image capturing platform 14. The movement of the arm section 13 in up and down directions is controlled by an arm section controller 31 built in the based 11.

The image capturing platform 14 includes, inside thereof, a radiation image detector 15, such as a flat panel detector or the like, and a detector controller 33 for controlling the reading of a charge signal from the radiation image detector 15 and the like.

The image capturing platform 14 further includes, inside thereof, a circuit board having thereon a charge amplifier for converting a charge signal read from the radiation image detector 15 to a voltage signal, a correlated double sampling circuit for sampling voltage signals outputted from the charge amplifier, an AD converter for converting the voltage signals to digital signals, and the like.

Radiation image detector 15 allows repeated use for recording and reading of radiation images, and a so-called direct type radiation image detector that generates a charge by directly receiving radiation or a so-called indirect type radiation image detector that converts radiation first to visible light and then converts the visible light to a charge signal may be used as the radiation image detector 15. As for the radiation image signal reading method, a so-called TFT (thin film transistor) reading method in which a radiation image signal is read by ON/OFF switching thin film transistors and a so-called optical reading method in which a radiation image signal is read by illuminating reading light are preferably used, but other method may also be used.

The radiation source unit 16 includes, inside thereof, a radiation source 17 and a radiation source controller 32. The radiation source controller 32 controls the emission timing of radiation from the radiation source 17 and the generation conditions of radiation (tube current, duration, tube voltage, and the like) in the radiation source 17.

Further, a compression paddle 18 disposed above the image capturing platform 14 for holding and compressing a breast, a support 20 for supporting the compression paddle 18, and a moving mechanism 19 for moving the support 20 in an up-down direction (Z direction) are provided on a central portion of the arm section 13. The position of compression paddle 18 and compression pressure are controlled by a compression paddle controller 34.

Further, a face guard 21 is provided on a surface of the radiation source unit 16 on the side of subject M through a support member 22 for preventing radiation from being applied to the face and neck of the subject M. The face guard 21 is a plate-like guard formed using a lead or copper member that absorbs radiation and radiation image capturing is performed with the face of the subject M being pressed against the face guard 21. By pressing the face of the subject M against the face guard 21, the subject M is prevented from being exposed to radiation as described above and the body posture of the subject M may be stabilized. As for the material of the face guard 21, lead-containing glass and resin (acrylic resin) may be used. In the case where such a material is used, the face guard 21 may be made transparent and an advantageous effect of providing a sense of security to the subject may be obtained.

Figure 2:
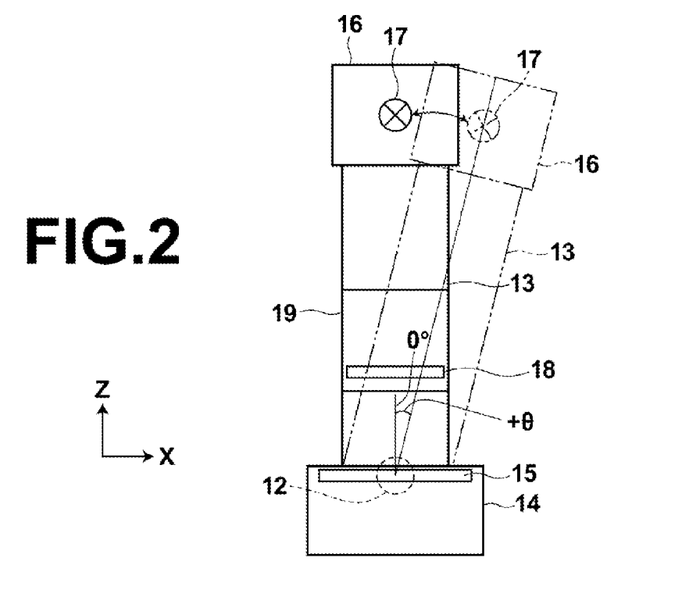
FIG. 2 illustrates a state in which the radiation source unit is moved in the breast image capturing and display system shown in FIG. 1.

Here, the breast image capturing apparatus 10 is an apparatus that performs stereoscopic image capturing in which a breast of the subject M is imaged from two different image capturing directions. When the stereoscopic image capturing is performed, the arm section 13 is rotated around the rotary shaft 12 and the radiation source unit 16 is moved in a left-right direction in front of the subject M, as illustrated in FIG. 2. Here, if the face guard 21 is moved in a left-right direction in conjunction with the radiation source unit 16, the body posture of the subject M becomes instable because the face of the subject M remains pressed against the face guard 21 as described above.

Consequently, an arrangement may be adopted in which the position of the face guard 21 remains unchanged even when the radiation source unit 16 is moved in a left-right direction in the breast image capturing apparatus 10 of the present embodiment. That is, the face guard 21 is configured to be movable relative to the radiation source unit 16.

When radiation image capturing is performed, it is necessary that the face guard 21 is moved relative to the radiation source unit 16, as described above, but if the face guard 21 is configured to move even when no radiation image capturing is performed, the face guard 21 will be moved unnecessarily which is undesirable from the viewpoint of user friendliness and durability.

Consequently, in the breast image capturing apparatus 10 of the present embodiment, the face guard 21 is configured to be movable relative to the radiation source unit 16 when radiation image capturing is performed, i.e., when the face of the subject M is abutted to the face guard 21 and to be fixed with respect to the radiation source unit 16 when radiation image capturing is not performed, i.e., when the face of the subject M is not abutted to the face guard 21. A specific configuration will be described hereinafter.

Figure 3:
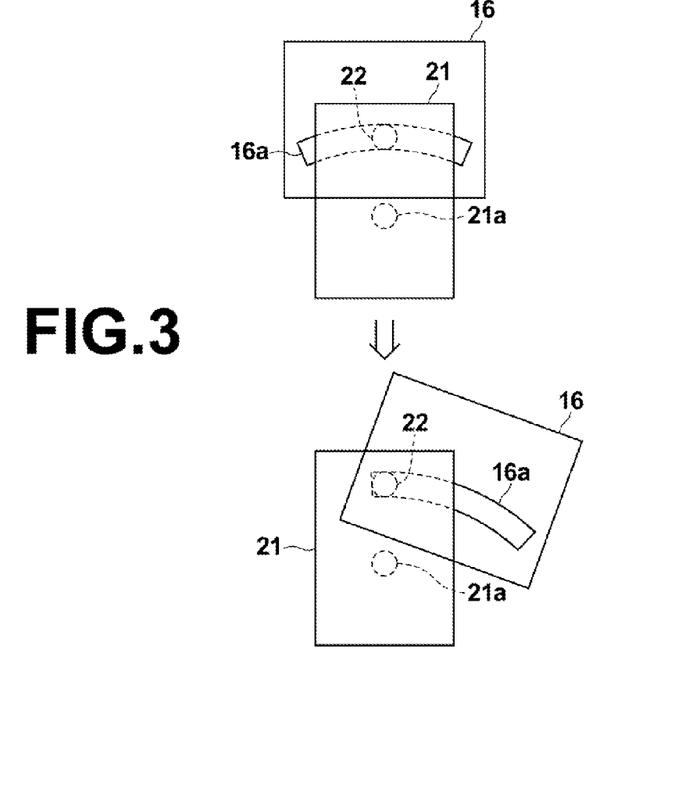
FIG. 3 illustrates an example relationship between the movement of the radiation source unit and the position of the face guard.

First, as illustrated in FIG. 3, an opening 16a is formed in the surface of the housing of the radiation source unit 16 on which the face guard 21 is mounted to allow the support member 22 supporting the face guard 21 to pass through so that the radiation source unit 16 is movable with the position of the face guard 21 being fixed.

The support member 22 supporting the face guard 21 is movably mounted inside of the radiation source unit 16 relative to the radiation source unit 16 according to the movement of the radiation source unit 16.

Figure 4:
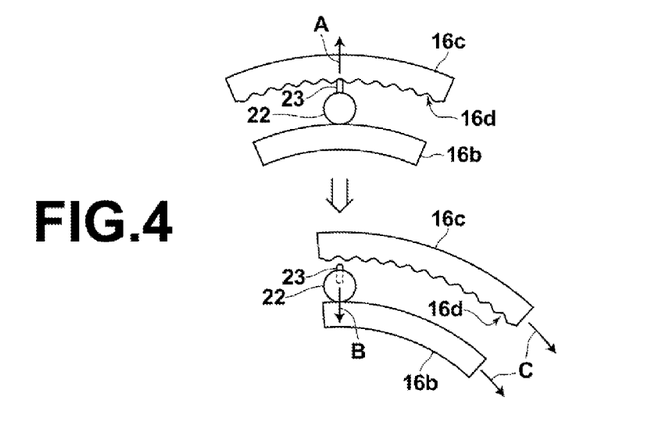
FIG. 4 illustrates an example of specific arrangement for controlling the movement of the face guard.

An arc-shaped rail member 16b and a grooved member 16c, as illustrated in FIG. 4, are fixedly mounted inside of the radiation source unit 16 so as to sandwich the support member 22 from the upper and lower sides. The support member 22 of the face guard 21 is moved slidingly on the rail member 16b. As illustrated in FIG. 4, grooves 16d are formed in the surface of the grooved member 16c on the side of the support member 22. The support member 22 is formed to move freely on the rail member 16b and no particular drive means for moving the support member is provided.

As illustrated in FIG. 3, the face guard 21 is provided with a contact sensor 21a for detecting that the face of the subject M is brought into contact with the face guard 21. As for the contact sensor 21a, for example, a sensor using a piezoelectric device may be employed.

As illustrated in FIG. 4, the support member 22 of the face guard 21 is provided with a latch 23 which protrudes from and retracts into the support member 22 based on a result of the detection by the contact sensor 21a described above. The latch 23 is formed with such a length as to engage with a groove 16d of the grooved member 16c provided upper side of the support member 22 when protruded from the support member 22 and not to engage with a groove 16d of the grooved member 16c when retracted into the support member 22. The operation of the latch 23 will be described later in detail.

Figure 5:
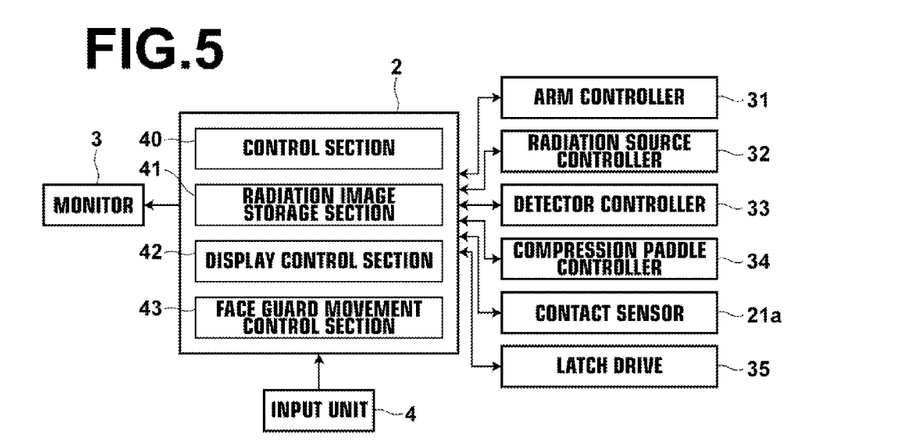
FIG. 5 is an internal block diagram of the computer of the breast image capturing and display system shown in FIG. 1, illustrating a schematic configuration thereof.

The computer 2 shown in FIG. 1 includes a central processing unit (CPU) and a storage device, such as a semiconductor memory, hard disk, SSD, or the like, and a control section 40, a radiation image storage section 41, a display control section 42, and a face guard movement control section 43, as illustrated in FIG. 5, are formed by the hardware described above.

The control section 40 outputs a predetermined control signal to each of the controllers 31 to 34 and performs control over the entire system. A specific control method will be described later in detail.

The radiation image storage section 41 stores image signals of two radiation images detected by the radiation image detector 15 through image capturing from two different image capturing directions.

The display control section 42 performs predetermined signal processing on the radiation image signals read from the radiation image storage section 41 and displays a stereo image of the breast on the monitor 3.

The latch drive 35 shown in FIG. 5 is a latch drive for driving the latch 23 shown in FIG. 4 and is provided in the radiation source unit 16. The latch drive 35 drives the latch 23 based on a control signal from the face guard movement control section 43. As for the latch drive 35, any known actuator may be used.

The input unit 4 shown in FIG. 1 is constituted by a pointing device, such as a keyboard or a mouse and accepts input from the radiographer, such as image capturing condition, image capturing start instruction, and the like.

The monitor 3 shown in FIG. 1 is a monitor configured to be able to display a stereos image using image signals of two radiation images outputted from the computer 2. As for the arrangement for displaying a stereo image, for example, an arrangement may be adopted in which two screens are used to display radiation images based on image signals of the two radiation images respectively, and one of the radiation images is inputted to the right eye of the observer while the other of which is inputted to the left eye of the observer using half mirrors or polarization glasses, thereby displaying a stereo image . Otherwise, for example, an arrangement may be adopted in which two radiation images are superimposed on top of each other and displayed by shifting a predetermined amount of parallax, and a stereo image is generated by observing the superimposed images with polarization glasses. Still further, an arrangement may be adopted in which a stereos image is generated by displaying two radiation images on a 3D liquid crystal capable of providing stereoscopic vision as in the parallax barrier method or lenticular process.

Figure 6:
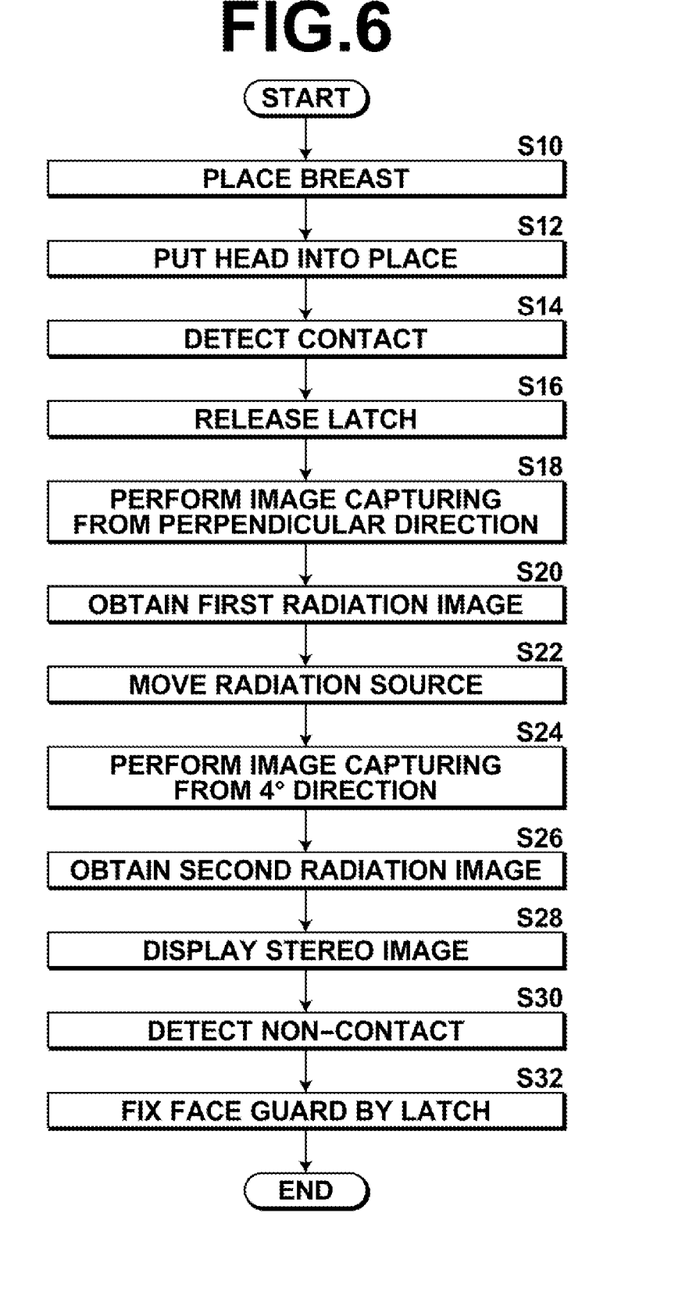
FIG. 6 is a flowchart for explaining an operation of the breast image capturing and display system that uses an embodiment of the breast image capturing apparatus of the present invention.

An operation of the breast image capturing and display system of the present embodiment will now be described with reference to the flowchart shown in FIG. 6.

First, a breast of the subject M is placed on the image capturing platform 14 and the breast is compressed at a predetermined pressure by a compression paddle 18 (S10), and the head of the subject M is pressed against the face guard 21 and put into place (S12).

Here, before the head of the subject M is pressed against the face guard as described above, the latch 23 is in a state of engagement with a groove 16d of the grooved member 16c by protruding from the support member 22 supporting the face guard 21 in a direction indicated by the arrow "A", as illustrated in FIG. 4, whereby the support member 22 and face guard 21 are fixed to the radiation source unit 16.

Then, when the head of the subject M is pressed against the face guard 21 as described above, the contact sensor 21a provided on the face guard 21 detects that the face of the subject M is brought into contact with the face guard 21 (S14), and a detection signal indicating the face contact is outputted to the face guard movement control section 43 of the computer 2.

When the detection signal indicating the face contact is inputted, the face guard movement control section 43 drives the latch drive 35 in response to the input to move the latch 23 in a direction indicated by the arrow "B", whereby the latch 23 is retracted into the support member 21 of the face guard 21 . The release of the latch 23 causes the support member 22 to be movably supported (S16).

Next, when an instruction to start image capturing is given by the radiographer through the input unit 4, image capturing for one of the two radiation images for generating a stereo image is performed (S18).

More specifically, the control section 40 reads preset image capturing angles θ for obtaining a stereo image and outputs the imaging angles θ to the arm section controller 31 first . In the present embodiment, it is assumed that, as the imaging angles θ, θ=0° and θ=4° are stored in advance, but the angles are not limited to these and any image capturing angles may be set by the radiographer through the input unit 4.

The information of the image capturing angles θ=0° and θ=4° outputted from the control section 40 is received by the arm section controller 31, and the arm section controller 31 first outputs a control signal for causing the arm section 13 to be oriented in a direction perpendicular to the image capturing platform 14, as illustrated in FIG. 2, based on the information of θ=0°.

Then, in the sate in which the arm section 13 is oriented in a direction perpendicular to the image capturing platform 14, the control section 40 outputs control signals to the radiation source controller 32 and detector controller 33 to perform radiation emission and radiation image signal reading respectively. In response to the control signals, radiation is emitted from the radiation source 17 and a radiation image of the breast captured from the 0° direction is detected by the radiation image detector 15. Then a signal of the radiation image is read by the detector controller 33 and stored in the radiation image storage section 41 after being subjected to predetermined signal processing (S20).

Next, image capturing for the second image of the two radiation images for generating a stereo image is performed.

More specifically, the arm section controller 31 outputs a control signal for causing the arm section 13 to be rotated by +θ° with respect to a direction perpendicular to the image capturing platform 14, as illustrated in FIG. 2. That is, in the present embodiment, the arm section controller 31 outputs a control signal for causing the arm section 13 to be rotated by +4° with respect to the direction perpendicular to the image capturing platform 14.

Based on the control signal outputted from the arm section controller 31, the arm section 13 is moved to the direction of 4° and, along with this, the radiation source unit 16 is also moved to the direction of 4° (S22). Here, the support member 22 of the face guard 21 is movably supported with respect to the radiation source unit 16 as described above, the support member 22 of the face guard 21 is not moved in conjunction with the radiation source unit 16 although the rail member 16b and grooved member 16c fixedly mounted in the radiation source unit 16 are moved in a direction indicated by the arrow "C" in conjunction with the radiation source unit 16, as illustrated in the lower side of FIG. 4. Thus, the face guard 21 is also not moved in conjunction with the radiation source unit 16 and the state in which the face of the subject M is pressed against the face guard 21 is maintained and hence the body posture of the subject M is also maintained.

Then, in the sate in which the arm section 13 is rotated by 4°, the control section 40 outputs control signals to the radiation source controller 32 and detector controller 33 to perform radiation emission and radiation image signal reading respectively. In response to the control signals, radiation is emitted from the radiation source 17 and a radiation image of the breast captured from the 4° direction is detected by the radiation image detector 15. Then a signal of the radiation image is read by the detector controller 33 and stored in the radiation image storage section 41 after being subjected to predetermined signal processing (S24, S26).

Then signals of two radiation images stored in the radiation image storage section 41 are read and outputted to the monitor 3 after being subjected to predetermined processing in the display control section 42, and a radiation image for right eye and a radiation image for left eye are displayed on the monitor 3, whereby a stereo image of the breast is displayed (S28).

Thereafter, when the stereo image capturing described above is completed, the arm section 13 is returned to the direction of 0°, the compression of the breast by the compression paddle 18 is released, and the head of the subject M is removed from the face guard 21. This causes the contact sensor 21a provided on the face guard 21 to detect that the face of the subject M is not in contact with the face guard 21, and a detection signal indicating the non-contact is outputted to the face guard movement control section 43 of the computer 2 (S30).

When the detection signal indicating the non-contact is inputted, the face guard movement control section 43 drives the latch drive 35 in response to the input to move the latch 23 in a direction indicated by the arrow "A", whereby the latch 23 is protruded from the support member 22 of the face guard 21, as illustrated in the upper side of the FIG. 4. Then, the protruded latch 23 engages with the grooved member 16c and the support member 22 is fixed to the radiation source unit 16, whereby the face guard 21 is fixed to the radiation source unit 16 (S32).

In the aforementioned embodiment, an arrangement is adopted in which a face abutment to the face guard 21 is detected by the contact sensor 21a and the movement of the face guard 21 is controlled by the detection result, but a sensor for detecting a face contact is not necessarily provided and the movement of the face guard 21 may be controlled by a mechanical arrangement.

Figure 7:
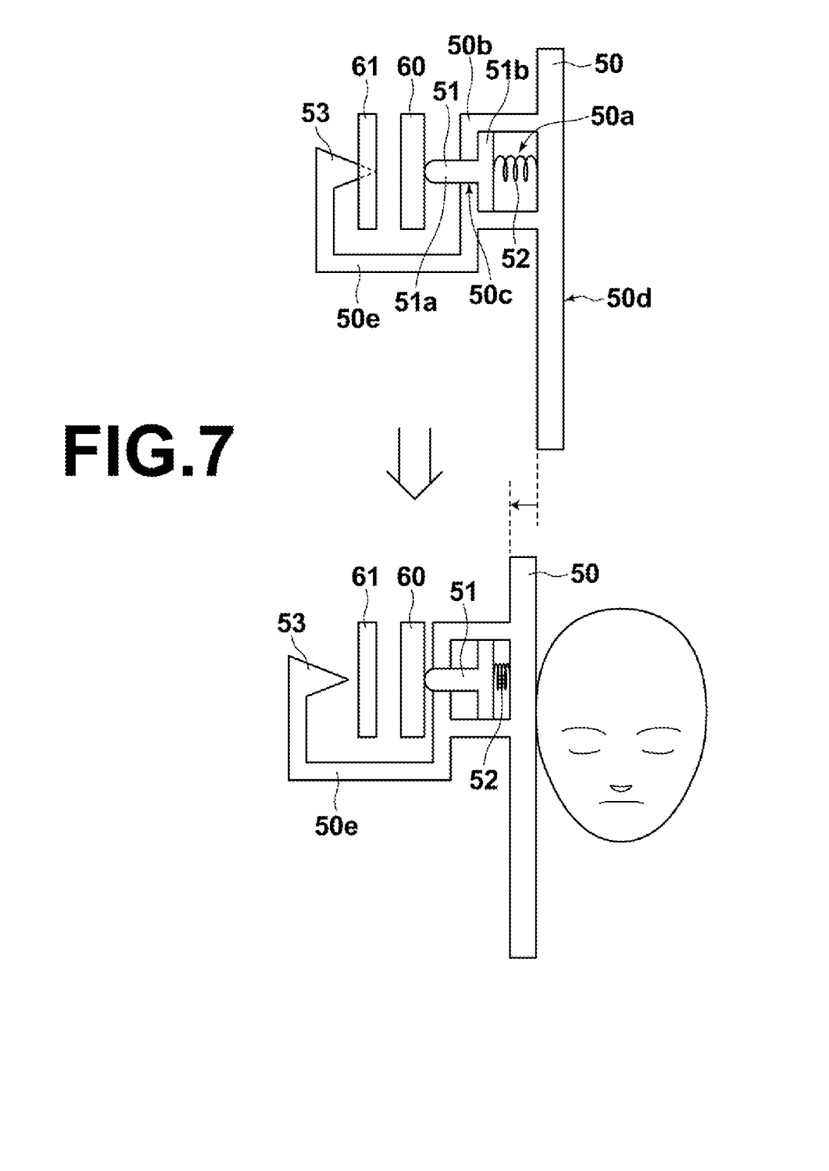
FIG. 7 illustrates an example of specific alternative arrangement for controlling the movement of the face guard.

More specifically, for example, an arrangement may be adopted in which a face guard 50 is provided with a support member 51, a spring member 52 connected to the support member 51, and a latch 53, in addition to a rail member 60 and a grooved member 61 provided in parallel to the face guard 50 in vertical direction inside of the radiation source unit 16, as illustrated in FIG. 7.

The rail member 60 and grooved member 61 are formed in an arc shape that conforms to the movement path of the radiation source unit 16, and vertical grooves are formed in the surface of the grooved member 61 on the side opposite to the face guard 50.

The support member 51 includes a pillar section 51a and a plate section 51b. The tip of the pillar section 51a is formed in a hemispherical shape so as to be slidingly movable on the rail member 60. The spring member 52 is connected to the plate section 51b and the spring member 52 is structured to bias the face guard 50.

The face guard 50 includes a housing section 50a, and the plate section 51b of the support member 51 and the spring member 52 are housed in the housing section 50a. A through hole 50c is formed in the face 50b of the housing section 50a and the pillar section 51a is formed so as to penetrate through the through hole 50c. Although the face guard 50 is biased in a direction away from the plate section 51b by the spring member 52 connected to the plate section 51b of the support member 51 as described above, the spacing between the face guard 50 and the plate section 51b becomes a predetermined distance by the abutment between the face 50b of the housing section 50a and the plate section 51b of the support member 51.

The face guard 50 further includes a member 50e extending to a direction opposite to a face 50d where the face of the subject M contacts and the latch 53 is formed on the tip of the member 50e. The biasing of the face guard 50 by the spring member 52 causes the member 50e and the latch 53 to be integrally biased and the latch 53 is formed to engage with a groove of the grooved member 61 by this.

As illustrated in the lower side of FIG. 7, when the face of the subject M is pressed against the face guard 50, the spring member 52 contracts by the pressing force, which causes the face guard 50, member 50e, and latch 53 to be integrally moved to the left direction in FIG. 7, i.e., in the direction in which the latch 53 is pulled away from the grooved member 61. This movement causes the engagement of the latch 53 with the grooved member 61 to be released and the face guard 50 is made movable relative to the radiation source unit 16. In this arrangement, when the engagement of the latch 53 with the grooved member 61 is released, the face guard 50 is supported so as to be movable freely and no particular drive means for moving the face guard 50 is provided.

Thereafter, when the face of the subject is removed from the face guard 50, the face guard 50 returns to the state illustrated in the upper side of FIG. 7, and the face guard 50 is fixed to the radiation source unit 16 by the engagement of the latch 53 with the grooved member 61.

The spring member 52 is used in the mechanical arrangement described above, but other elastic members, such as an elastic rubber member, may be used.

The mechanical arrangement is not limited to the aforementioned arrangement, and any other mechanical arrangement may be used as long as it allows the face guard to be movable relative to the radiation source unit during the face of the subject M is abutted to the face guard and to be fixed while the face of the subject M is not abutted to the face guard.

The embodiment described above is an embodiment in which the breast image capturing apparatus of the present invention is applied to a stereo breast image capturing apparatus, but the invention is not limited to this and the present invention is applicable to any other apparatus as long as it performs radiation image capturing from a plurality of image capturing directions by moving the radiation source in a left-right direction in front of the subject . Such apparatuses may include, for example, tomosynthesis image capturing equipment.

Further, in the aforementioned embodiment, the movement of the face guard 21 with respect to the arm section 13 is controlled according to whether or not the face is abutted to the face guard 21. But the arrangement is not limited to this and the movement of the face guard 21 with respect to the arm section 13 may be controlled, for example, according to the ON/OFF of the power of the radiation source 17.

That is, if the radiation source 17 is in a power-off state, it means that the apparatus is not performing radiation image capturing and hence it is desirable that the face guard 21 is fixed with respect to the arm section 13. Therefore, an arrangement may be adopted in which the face guard movement control section 43 obtains the information that the radiation source 17 is in a power-off state and controls such that the face guard 21 is fixed with respect to the arm section 13 based on the information. Note that the arm section 13 itself is movable for performing various adjustments and the like.

On the other hand, if the radiation source 17 is in a power-on state, it means that the apparatus is performing radiation image capturing and hence it is desirable that the face guard 21 is supported movably with respect to the arm section 13. Therefore, an arrangement may be adopted in which the face guard movement control section 43 obtains the information that the radiation source 17 is in a power-on state and controls such that the face guard 21 is supported movably with respect to the arm section 13 based on the information.

What is claimed is:
1. A breast image capturing apparatus comprising:
   a radiation application section which includes an arm section for moving a radiation source in a left-right direction in front of a subject and applies radiation to a breast of the subject from different image capturing directions above the breast through the movement of the radiation source by the arm section; and
   a radiation image detector that detects a radiation image generated through the application of radiation by the radiation application section with respect to each of the image capturing directions: and a shielding member for preventing the radiation from being applied to the face of the subject is provided on the arm section, wherein the shielding member is configured so as to be movably supported relative to the arm section when the face of the subject is abutted to the shielding member and fixedly supported relative to the arm section when the face of the subject is not abutted to the shielding member, the apparatus comprises a latch for controlling the movement of the shielding member by engaging with a predetermined member, the latch is a latch that does not engage with the member when the face of the subject is abutted to the shielding member and engages with the member when the face of the subject is not abutted to the shielding member, and the apparatus includes:

a sensor for detecting that the face of the subject is in contact with the shielding member; and a latch drive for driving the latch according to a result of the detection by the sensor.

2. The breast image capturing apparatus of claim 1, wherein the shielding member is a shielding member that, while the face of the subject is abutted to the shielding member, does not move from the position of the face of the subject.

3. The breast image capturing apparatus of claim 1, wherein a grooved member having a groove that engages with the latch is fixedly installed relative to the arm section.

4. A breast image capturing apparatus comprising:

a radiation application section which includes an arm section for moving a radiation source in a left-right direction in front of a subject and applies radiation to a breast of the subject from different image capturing directions above the breast through the movement of the radiation source by the arm section; and a radiation image detector that detects a radiation image generated through the application of radiation by the radiation application section with respect to each of the image capturing directions; and a shielding member for preventing the radiation from being applied to the face of the subject is provided on the arm section, wherein the shielding member is configured so as to be movably supported relative to the arm section when the face of the subject is abutted to the shielding member and fixedly supported relative to the arm section when the face of the subject is not abutted to the shielding member, the apparatus comprises a latch for controlling the movement of the shielding member by engaging with a predetermined member, the latch is a latch that does not engage with the member when the face of the subject is abutted to the shielding member and engages with the member when the face of the subject is not abutted to the shielding member, and the latch is a latch whose engagement with the member is released by a force generated by the abutment of the face of the subject to the shielding member.

5. The breast image capturing apparatus of claim 4, wherein:

the apparatus comprises an elastic member that expands or contracts according to whether or not the face of the subject is abutted to the shielding member; and the latch is a latch that engages with or disengages from the member by the expansion or contraction of the elastic member.

6. The breast image capturing apparatus of claim 4, wherein the shielding member is a shielding member that, while the face of the subject is abutted to the shielding member, does not move from the position of the face of the subject.

7. The breast image capturing apparatus of claim 4, wherein a grooved member having a groove that engages with the latch is fixedly installed relative to the arm section.

\* \* \* \* \*